US00PP26397P2

(12) United States Plant Patent
Dummen

(10) Patent No.: US PP26,397 P2
(45) Date of Patent: Feb. 2, 2016

(54) ***CALIBRACHOA* PLANT NAMED 'DUEVOLGO'**

(50) Latin Name: ***Calibrachoa* sp.**
Varietal Denomination: Duevolgo

(71) Applicant: Tobias Dummen, Rheinberg (DE)

(72) Inventor: Tobias Dummen, Rheinberg (DE)

(73) Assignee: Dümmen Group B.V., DeLier (NL)

( * ) Notice: Subject to any disclaimer, the term of this patent is extended or adjusted under 35 U.S.C. 154(b) by 0 days.

(21) Appl. No.: 14/120,810

(22) Filed: Jul. 1, 2014

(51) Int. Cl.
*A01H 5/02* (2006.01)

(52) U.S. Cl.
USPC ..... Plt./413

(58) Field of Classification Search
USPC ..... Plt./413
CPC ..... A01H 5/02; A01H 5/00
See application file for complete search history.

*Primary Examiner* — Kent L Bell
(74) *Attorney, Agent, or Firm* — C.A. Whealy

(57) ABSTRACT

A new and distinct cultivar of *Calibrachoa* plant named 'Duevolgo', characterized by its compact, semi-upright and outwardly spreading to trailing and decumbent plant habit; freely branching habit; early and freely flowering habit; large bright yellow-colored flowers with dark orange red-colored centers and venation; and good garden performance.

1 Drawing Sheet

Botanical designation: *Calibrachoa* sp.
Cultivar denomination: 'DUEVOLGO'.

BACKGROUND OF THE INVENTION

The present invention relates to a new and distinct cultivar of *Calibrachoa* plant, botanically known as *Calibrachoa* sp. and hereinafter referred to by the name 'Duevolgo'.

The new *Calibrachoa* plant is a product of a planned breeding program conducted by the Inventor in Rheinberg, Germany. The objective of the breeding program is to create new compact *Calibrachoa* plants with large attractive flowers.

The new *Calibrachoa* plant originated from a cross-pollination made by the Inventor in July, 2011 in Rheinberg, Germany of a proprietary selection of *Calibrachoa* sp. identified as code number A10-1240-004, not patented, as the female, or seed, parent with a proprietary selection of *Calibrachoa* sp. identified as code number A10-0340-008, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2013.

Asexual reproduction of the new *Calibrachoa* plant by vegetative terminal cuttings in a controlled greenhouse environment in Rheinberg, Germany since June, 2013 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duevolgo'.

These characteristics in combination distinguish 'Duevolgo' as a new and distinct *Calibrachoa* plant:

1. Compact, semi-upright and outwardly spreading to trailing and decumbent plant habit.
2. Freely branching habit.
3. Early and freely flowering habit.
4. Large bright yellow-colored flowers with dark orange red-colored centers and venation.
5. Good garden performance.

The new *Calibrachoa* can be compared to plants of the female parent selection. Plants of the new *Calibrachoa* differ primarily from plants of the female parent selection in branching habit as plants of the new *Calibrachoa* are more freely branching than plants of the female parent selection. In addition, plants of the new *Calibrachoa* have lighter-colored flowers than plants of the female parent selection.

The new *Calibrachoa* can be compared to plants of the male parent selection. Plants of the new *Calibrachoa* differ primarily from plants of the male parent selection in flower color as plants of the male parent selection have red-colored flowers. In addition, plants of the new *Calibrachoa* have smaller flowers than plants of the male parent selection.

Plants of the new *Calibrachoa* can also be compared to plants of *Calibrachoa* sp. 'Cal Yel', disclosed in U.S. Plant Pat. No. 14,464. In side-by-side comparisons, plants of the new *Calibrachoa* differed primarily from plants of 'Cal Yel' in the following characteristics:

1. Plants of the new *Calibrachoa* were more compact than plants of 'Cal Yel'.
2. Plants of the new *Calibrachoa* had shorter and slightly broader leaves than plants of 'Cal Yel'.
3. Plants of the new *Calibrachoa* and 'Cal Yel' differed in flower color as plants of 'Cal Yel' had darker yellow-colored flowers.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant.

The photograph is a side perspective view of a typical flowering plant of 'Duevolgo' grown in a container.

DETAILED BOTANICAL DESCRIPTION

The aforementioned photograph and following observations, measurements and values describe plants grown during the summer in 30-cm containers in a glass-covered greenhouse in Rheinberg, Germany and under cultural practices typical of commercial *Calibrachoa* production. During the production of the plants, day and night temperatures averaged 18° C. and light levels averaged 4,500 lux. Rooted young plants were pinched one time three weeks after planting and were 13 weeks old when the photograph and description were taken. In the following description, color references are made to The Royal Horticultural Society Colour Chart, 2007 Edition, except where general terms of ordinary dictionary significance are used.

Botanical classification: *Calibrachoa* sp. 'Duevolgo'.

Parentage:

- *Female, or seed, parent.*—Proprietary selection of *Calibrachoa* sp. identified as code number A10-1240-004, not patented.
- *Male, or pollen, parent.*—Proprietary selection of *Calibrachoa* sp. identified as code number A10-0340-008, not patented.

Propagation:

- *Type.*—By vegetative cuttings.
- *Time to initiate roots, summer.*—About five days at temperatures about 20° C.
- *Time to initiate roots, winter.*—About seven days at temperatures about 20° C.
- *Time to produce a rooted young plant, summer.*—About three weeks at temperatures about 20° C.
- *Time to produce a rooted young plant, winter.*—About four weeks at temperatures about 20° C.
- *Root description.*—Fine, fibrous; white in color.
- *Rooting habit.*—Freely branching; dense.

Plant description:

- *Plant and growth habit.*—Compact, semi-upright and outwardly spreading to trailing and decumbent plant habit; freely branching habit with about seven primary lateral branches developing per plant; pinching enhances branching; vigorous growth habit; moderate growth rate.
- *Plant height.*—About 20 cm.
- *Plant diameter.*—About 56 cm.

Lateral branch description:

- *Length.*—About 32.5 cm.
- *Diameter.*—About 2 mm.
- *Internode length.*—About 1.9 cm.
- *Strength.*—Strong.
- *Aspect.*—Initially upright to outwardly spreading to trailing and decumbent.
- *Texture.*—Pubescent.
- *Color.*—Close to 146C.

Leaf description:

- *Arrangement.*—Alternate, simple.
- *Length.*—About 2.1 cm.
- *Width.*—About 7.8 mm.
- *Shape.*—Oblanceolate.
- *Apex.*—Rounded.
- *Base.*—Cuneate.
- *Margin.*—Entire.
- *Texture, upper and lower surfaces.*—Pubescent.
- *Venation pattern.*—Pinnate; arcuate.
- *Color.*—Developing and fully expanded leaves, upper surface: Close to 146A; venation, close to 144C. Developing and fully expanded leaves, lower surface: Close to 146C; venation, close to 144C.
- *Petioles.*—Length: About 1.4 mm. Diameter: About 1 mm. Texture, upper and lower surfaces: Pubescent. Color, upper and lower surfaces: Close to 144C.

Flower description:

- *Flower arrangement and habit.*—Single salverform flowers arising from leaf axils; freely flowering habit with usually about 50 to 60 flowers developing per plant; flowers face upright or outwardly.
- *Fragrance.*—None detected.
- *Natural flowering season.*—Early flowering habit, plants of the new *Calibrachoa* initiate and develop flowers about four to five weeks after planting; plants flower continuously from the spring throughout the summer in Germany.
- *Flower longevity.*—Individual flowers last about seven to ten days on the plant; flowers not persistent.
- *Flower diameter.*—About 3.1 cm.
- *Flower length (height).*—About 1.6 cm.
- *Flower throat diameter.*—About 7.6 mm.
- *Flower tube length.*—About 1.7 cm.
- *Flower tube diameter, base.*—About 1.6 mm.
- *Flower buds.*—Length: About 1.6 cm. Diameter: About 2.8 mm. Shape: Elongated oblong. Color: Close to 4B.
- *Corolla.*—Arrangement: Five petals fused at the base and opening into a flared trumpet. Petal length from throat: About 2.8 cm. Petal lobe width: About 1.4 cm. Petal shape: Roughly spatulate. Petal apex: Mostly rounded to slightly retuse. Petal margin: Entire. Petal texture, upper and lower surfaces: Smooth, glabrous. Throat texture: Smooth, glabrous. Tube texture: Smooth, glabrous. Color: Petal, when opening and fully opened, upper surface: Close to 3A; towards the base and venation, close to N34A; main color becoming closer to 5B with development. Petal, when opening and fully opened, lower surface: Close to 3D; venation, close to N34A. Throat: Close to 7A; venation, close to N34A. Tube: Close to 3C; venation, close to N34A.
- *Calyx.*—Arrangement: Star-shaped calyx with five sepals; sepals fused at the base. Sepal length: About 1.3 cm. Sepal width: About 2.4 mm. Sepal shape: Lanceolate. Sepal apex: Acute. Sepal margin: Entire. Sepal texture, upper and lower surfaces: Pubescent. Color, upper and lower surfaces: Close to 138A.
- *Peduncles.*—Length: About 1.1 cm. Diameter: About 1 mm. Angle: About 45° from stem axis. Strength: Moderately strong. Texture: Pubescent. Color: Close to 145A.
- *Reproductive organs.*—Stamens: Quantity: Six per flower. Filament length: About 1.1 cm. Filament color: Close to 1C. Anther shape: Ellipsoidal. Anther length: About 1 mm. Anther color: Close to 15A. Pollen amount: Scarce. Pollen color: Close to 15A. Pistils: Quantity: One per flower. Pistil length: About 1.1 cm. Style length: About 6 mm. Style color: Close to 142B. Stigma shape: Ellipsoidal. Stigma color: Close to 141D. Ovary color: Close to 142B. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 5° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'Duevolgo' as illustrated and described.

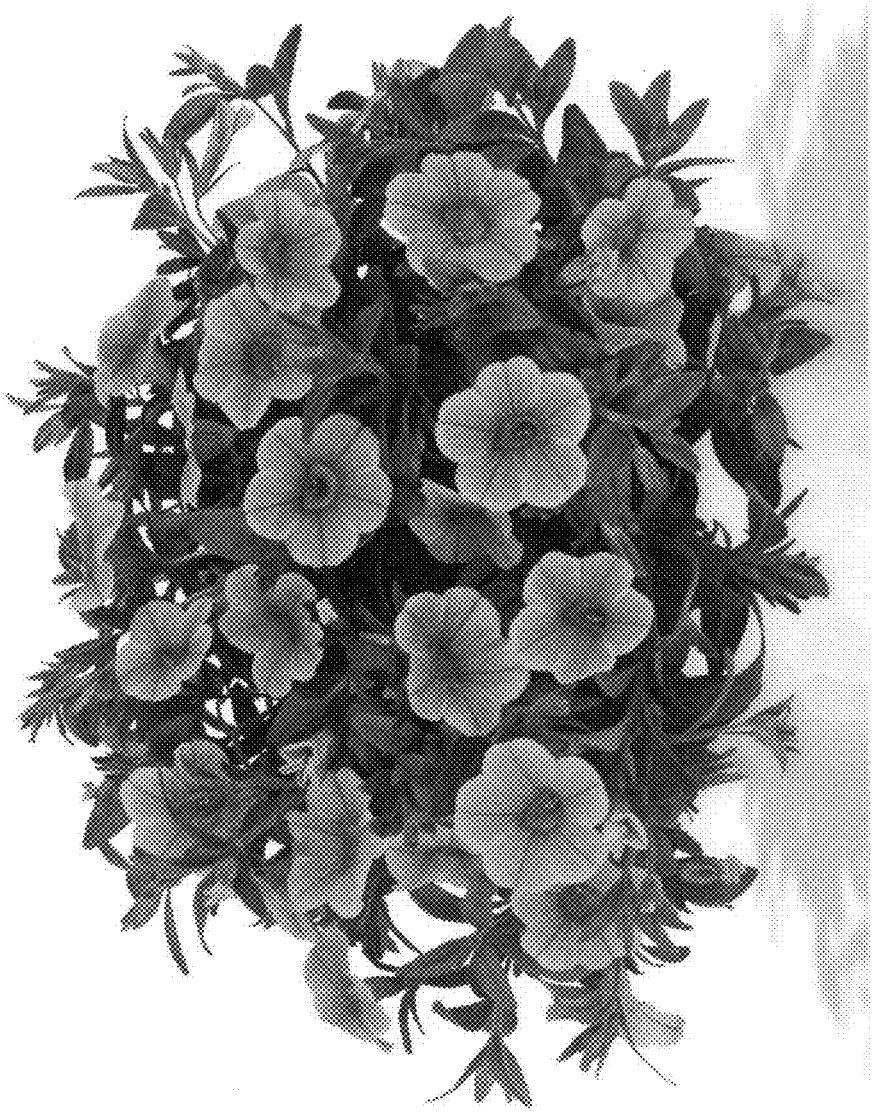

* * * * *